United States Patent [19]

Johansen

[11] Patent Number: 5,434,343
[45] Date of Patent: Jul. 18, 1995

[54] POTATO VARIETY 'ND1538-1RUSS'

[75] Inventor: Robert H. Johansen, Fargo, N. Dak.

[73] Assignee: North Dakota State University, Fargo, N. Dak.

[21] Appl. No.: 487,286

[22] Filed: Mar. 2, 1990

[51] Int. Cl.⁶ .......................... A01H 1/00; A01H 5/06
[52] U.S. Cl. ........................... 800/200; 800/DIG. 42; 47/58; 47/DIG. 1
[58] Field of Search ...................... 800/200, DIG. 42; 47/58, DIG. 1

[56] References Cited
U.S. PATENT DOCUMENTS

| 4,696,674 | 9/1987 | Cipar | 800/DIG. 42 |
| 4,723,052 | 2/1988 | Cochran | 800/DIG. 42 |
| 4,795,705 | 1/1989 | Gressel et al. | 800/DIG. 42 |

Primary Examiner—James R. Feyrer
Attorney, Agent, or Firm—M. Reid Russell

[57] ABSTRACT

The new potato variety Solanum tuberosum is a cross of a Lemhi and a ND450-3Russ. It was first grown at the Langdon Experiment Station, North Dakota. The new variety produces tubers that are long, smooth, and uniform with shallow eyes and dark brown skin that are suitable for fresh market. The variety is resistant to hollow heart and appears to be well adapted to the soils of the Mid-Western United States.

3 Claims, 4 Drawing Sheets

POTATO VARIETY 'ND1538-1RUSS'

BACKGROUND OF THE INVENTION

1. Field of the Invention

The present invention relates to a new and distinct variety of potato Solanum tuberosum which was discovered by me growing at the Langdon Experiment Station, North Dakota.

2. Prior Art

The new potato variety was produced from a cross made by me in the North Dakota State University horticulture greenhouse, Fargo, N. Dak., with a seedling tuber also produced in the North Dakota State University horticulture greenhouse. The new variety, ND1538-1Russ resulted from a cross between a Lemhi and a ND450-3Russ.

University colleagues, breeders and seedsmen who have seen this potato do not recognize this selection as anything that they have previously selected or evaluated. The potato variety has been classified as a cross of a Lemhi and ND450-3Russet. Selection and initial evaluation was done as set out above. Evaluations were done at the Langdon Experiment Station, North Dakota, and horticulture greenhouse of the North Dakota State University. Testing in variety trials at North Dakota State University began in 1986 and commercial trials were initiated in Grand Forks, N. Dak. in 1988.

BRIEF SUMMARY OF THE INVENTION

The plants of the new variety of potato hereinafter referred to as ND1538-1Russ are medium to slightly large in size and are somewhat upright. The stems are green and are purple near the base of the plants. The leaves are medium in size and are green to dark green in color. The flowers are light lavender to white. The base of the corolla is purple in color. The flowers are male and female fertile, however flowering in general is quite scant.

The tubers of ND1538-1Russ are oblong to quite long and have a fairly heavy russet skin. Shape can vary depending on the soil they are produced in. The tuber eyes are shallow with purple sprouts. After several months of storage a reddish tinge can be seen in the skin of the tubers. Yields of ND1538-1Russ at two locations in North Dakota for two years showed this variety to be much higher than standard russet variety, Russet Burbank, but comparable to NorKing Russet and slightly lower than Norgold Russet and Russet Norkotah.

ND1538-1Russ exhibits very little internal or external defects especially hollow heart. Hollow heart is an internal defect that makes a hollow center in the tuber. This defect cannot be detected unless the tuber is cut or is run through an X-ray machine that shows the hollow center. Hollow heart generally occurs after a tuber of a susceptible variety is exposed to rapid growth as occurs from excessive moisture following a dry period. Several varieties especially some of the russet varieties are very susceptible to hollow heart. In tests during a 3-year period ND1538-1Russ only showed from six (6) to two (2) percent hollow heart while Norgold Russet and several other russet type varieties showed from forty-nine (49) to twelve (12) percent hollow heart when grown in similar conditions. ND1538-1Russ appeared to be very resistant to hollow heart.

When evaluated for culinary qualities, ND1538-1Russ expressed excellent boiling and baking qualities. The flesh of ND1538-1Russ following cooking is especially white and attractive. ND1538-1Russ is comparable to Russet Burbank when tested for french fry qualities. Total solids are comparable to Norgold Russet but higher than Russet Burbank and Russet Norkotah. ND1538-1Russ has been increased by indexed disease-free tubers and by tissue culture. All increase of ND1538-1Russ has been done by foundation seed growers in North Dakota and Montana.

DETAILED DESCRIPTION

The following is a detailed description of the new variety of potato Solanum tuberosum, hereinafter referred to as ND1583-1Russ. Color terminology as set out herein is to be accorded its ordinary dictionary significance except where otherwise indicated. The tubers and plants described were grown at Casselton and Grand Forks, N. Dak.

Figure 1:
FIG. 1 shows as true as is reasonably possible, a plant and leaf type of ND1538-1Russ grown at Grand Forks, N. Dak.
Figure 2:
FIG. 2, shows as true as is reasonably possible, a flower of ND1538-1Russ, the corolla of which should be understood to be purplish.

Plant, as shown best in FIGS. 1 and 2: Medium to quite large, somewhat upright.

Stems: Green pigmented, purplish near base of the plant.

Wings: Medium in size reaching ½ or more of the entire way or distance to the next node.

Nodes: Not prominent.

Leaves: Medium in size compared to Russet Burbank and Russet Norkotah, but small compared to NorKing Russet and Norchip. Green to dark green, moderately pubescent. Open when young, open from maturity to senescence.

Terminal Leaflets: Elliptical; apex acuminate; base lobed to auriculate; asymmetrical; length 64 mm±0.105, width 37.0 mm=0.055, L-W 17.3±0.013.

Primary Leaflets: Ovate; apex acuminate; asymmetrical; 3 to 4 pairs. Length 64.0 mm±1.22, width 36.9±0.66, length to width 17.3±0.11.

Secondary Leaflets: Common.

Tertiary Leaflets: Common. Supernumerary secondary leaflets on petiole of secondary leaflets, common.

Midriffs and Petioles: Light green; sparsely pigmented; slightly pubescent.

Flowers: Sparse

Buds: Off-white or greenish white to light lavender.

Calyx: Long straight green pubescent, 18.32 mm.

Corolla: Large; light lavender to white; green midrib.

Anthers: Orange pollen abundant and of good quality.

Style: Curved.

Stigma: Roughly globose; multilobed and green.

Figure 3:
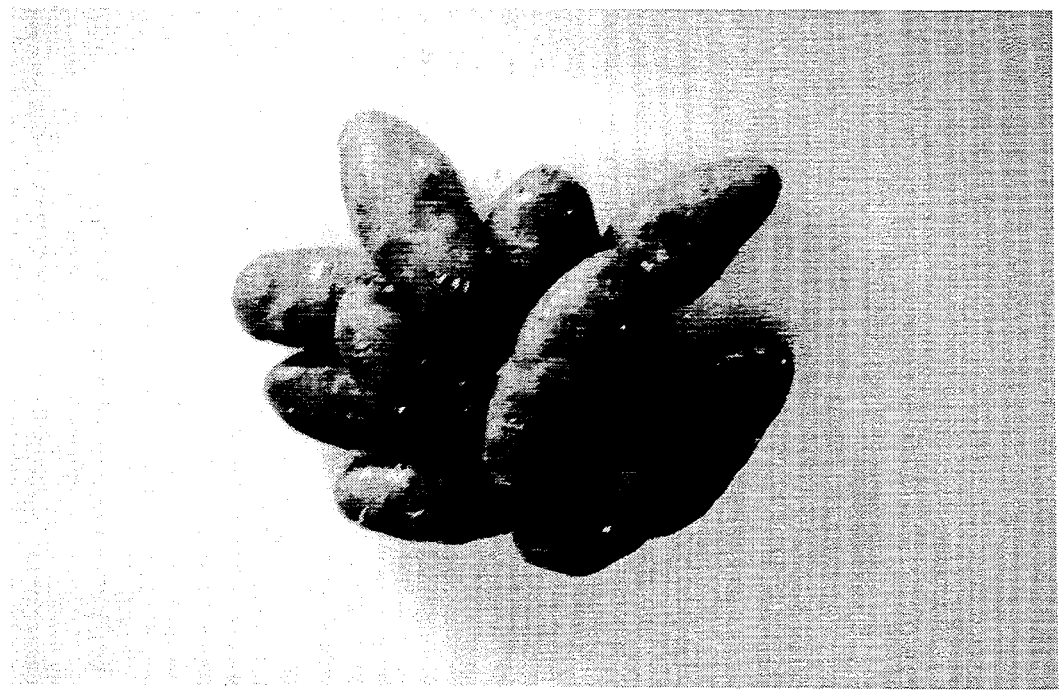
FIG. 3, shows as true as is reasonably possible, tubers of ND1538-1Russ grown at 1988 commercial trials at Grand Forks, N. Dak.

Tubers (as shown best in FIG. 3): Oblong to quite long; a 25 tuber sample was measured and found to have a mean length of 112 mm., a mean width of 63.9 mm, and a mean thickness of 55.0 mm.

Indices: Width to length 0.51; thickness to length 0.56; thickness to width 0.59; average number of tubers per plant 6–10.

Skin: Dark brown; fairly heavy russeted.

Eyes: Shallow; well distributed and fairly numerous.

Flesh: Very white.

Sprouts: White with purple tip.

Maturity: Medium; later than Russet Norkotah but much earlier than Russet Burbank.

Characteristics: Tubers are usually smooth and quite uniform, however ND1538-1Russ is not as smooth and uniform as Russet Norkotah. Off-shape tubers have been observed. After storage a reddish blush can be observed on the apical end of tubers. Very few external or internal defects have been observed, however ND1538-1Russ is almost free of the defect hollow heart.

Figure 4:
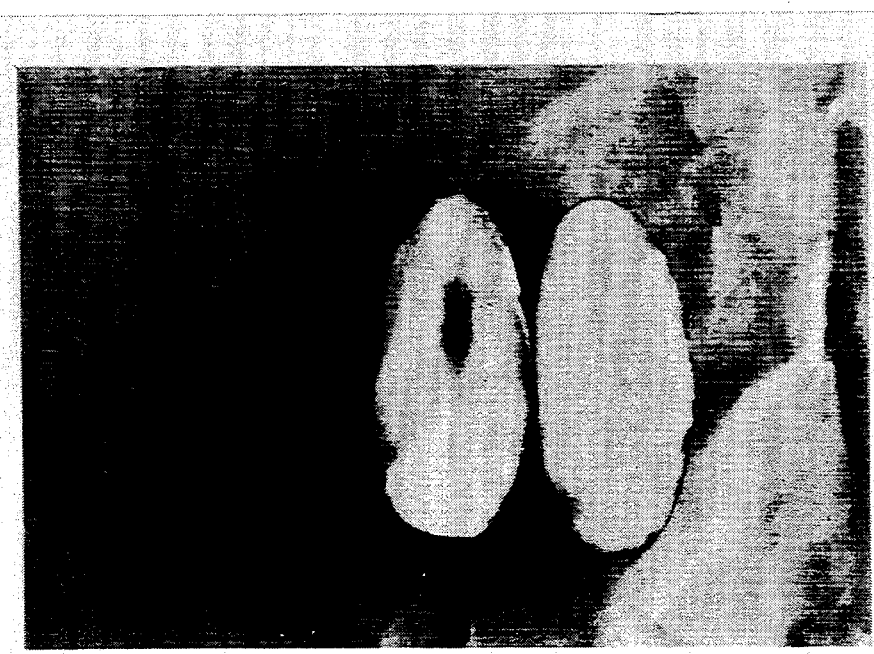
FIG. 4, shows as true as is reasonably possible, a Norgold Russet tuber infected with hollow heart cut longitudinally, bottom row.
Figure 5:
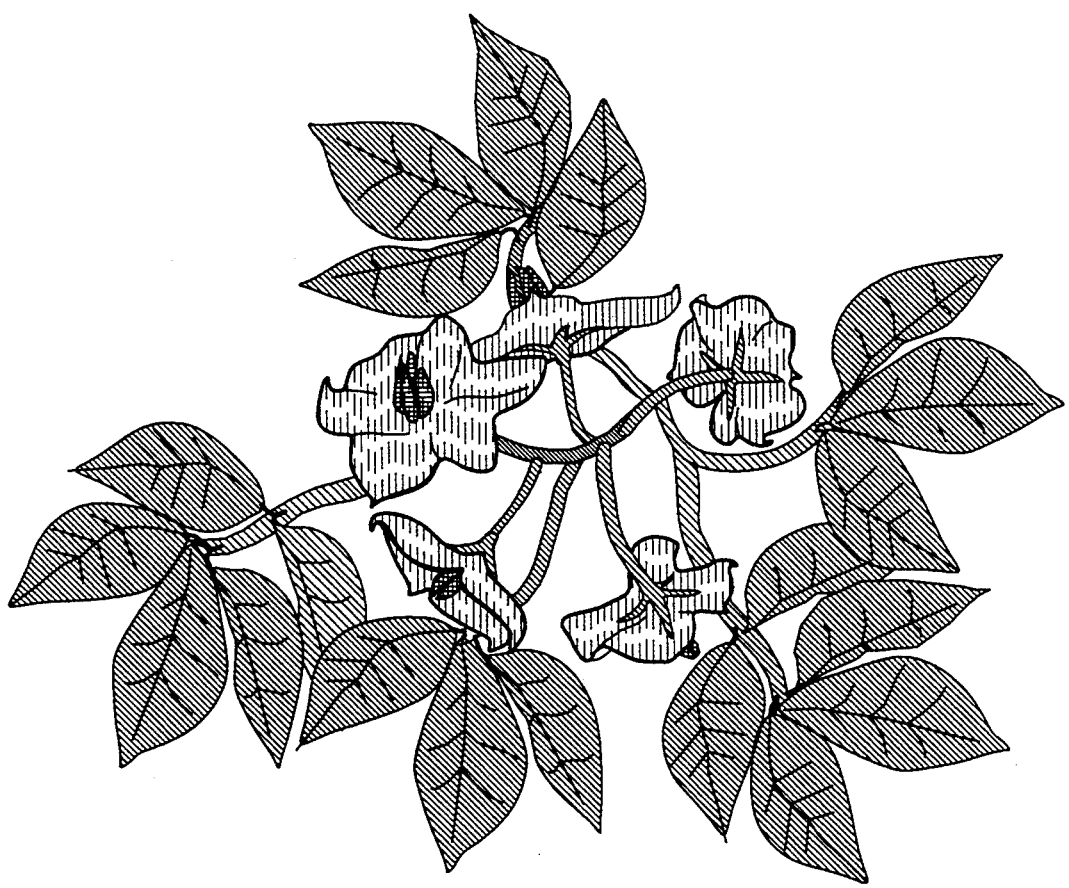
FIG. 5 is a mechanical drawing which shows the coloration of the plant by cross hatching; and, FIG. 6 is a flow chart which shows the pedigree of the plant of this invention through 5 generations. The arrows in the chart indicate the parents of the plant from which the arrow is drawn.
Figure 6:
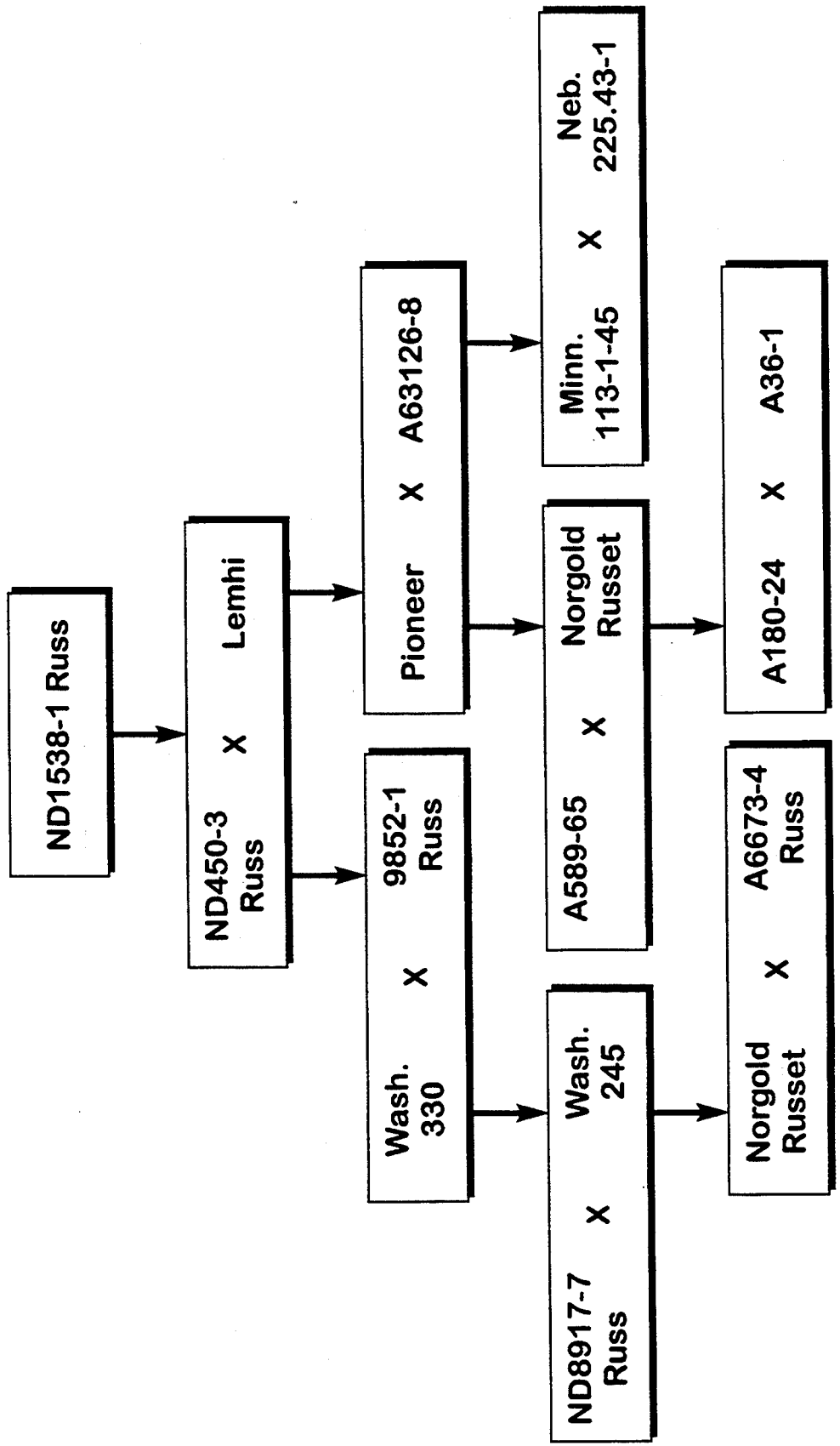

Uses: Because of ND1538-1Russ's hollow heart resistance, FIG. 4 shows a hollow heart infected Norgold Russet, it is accordingly a variety that can be grown and marketed as a count carton variety in the Red River Valley of North Dakota and Minnesota or other areas where hollow heart is a problem. This variety with its white flesh makes a very good variety for both mashing and baking, and can be used for french fries.

Yields: Two year tests at two locations in North Dakota have shown ND1538-1Russ to produce as good a yield as test plantings of NorKing Russet, and produced a higher yield than Russet Burbank. In the two year trials both Norgold Russet and Russet Norkotah had slightly greater yields than the tested ND1538-1Russ.

Disease Resistance: ND1538-1Russ expresses both plant and tuber symptoms when infected with bacterial ring rot.

A germ plasma of ND1538-1Russ, *Solanum tuberosum* to be deposited with the American Type Culture Collection (ATCC), Rockville, Md., accorded an Accession Number (ATCC) 75857C, deposited Aug. 10, 1994, which deposit is made under the conditions of the Budapest Treaty that provide that:

(a) during the pendency of this application access to the invention will be afforded to the Commissioner upon request;

(b) all restrictions upon available to the public will be revokable removed upon granting of a patent on this application;

(c) the deposit will be maintained in a public depository for a period of thirty (30) years, or five (5) years after the last request, or for the effective life of a patent issued on this application, whichever is longer; and (d) the deposit will be replaced should it become inviable.

A complete pedigree of ND1538-1Russ follows:

Identification of the Potato Varieties in the Parentage of ND1538-1Russ

1. *Lemhi Russet*—Named in Idaho in 1981. 155 acres grown for certification in the United States and Canada in 1988.

2. *Pioneer*—Named in Nebraska in 1963. No certified acres grown. Probably extinct.

3. *Norgold Russet*—Named in North Dakota in 1964. 1632 acres grown in the United States and Canada for certification in 1988. Was replaced by Russet Norkotah.

4. *Advanced Selections:*

---
ND450-3Russ
A63126-8
Wash. 330
ND9852-1Russ
Minn. 113-1-45
Neb. 225.43-1
A589-65
ND8917-7Russ
Wash. 245
A180-24
A36-1; and
A6673-4Russ
are all advanced selections that probably have been dropped from the breeding program or only maintained. They have not, and most probably will not, become varieties.

---

Legend for above advanced selections:
ND = North Dakota; A = Idaho USDA; Wash. = Washington; Minn. = Minnesota; Neb. = Nebraska.

TABLES

Herein are included Tables I, II, and III that detail ND1538-1Russ characteristics for, respectively: U.S. No. 1 yield and percent U.S. No. 1 in 1987 and 1988; percent total solids, 1987 and 1988, and percent hollow heart by weight, 1986–1988 for two locations in North Dakota.

TABLE I

U.S. No. 1 Yield and Percent U.S. No. 1 (Grand Forks and Park River, ND 1987–1988).

| | 1987 | | | | 1988 | | | | Average | |
|---|---|---|---|---|---|---|---|---|---|---|
| | Grand Forks | | Park River | | Grand Forks | | Park River | | | |
| | Cwt U.S. No. 1 | % U.S. No. 1 | Cwt U.S. No. 1 | % U.S. No. 1 | Cwt U.S. No. 1 | % U.S. No. 1 | Cwt U.S. No. 1 | % U.S. No. 1 | Cwt U.S. No. 1 | % U.S. No. 1 |
| ND1538-1Russ | 247 | 63 | 165 | 86 | 128 | 80 | 176 | 86 | 179 | 79 |
| NorKing Russet | 225 | 83 | 192 | 90 | 143 | 73 | 155 | 79 | 179 | 82 |
| Norgold Russet | 240 | 82 | 273 | 86 | 81 | 67 | 178 | 73 | 193 | 79 |
| Russet Burbank | 92 | 53 | 156 | 54 | 24 | 26 | 33 | 22 | 77 | 38 |
| Russet Norkotah | 261 | 87 | 232 | 95 | 85 | 77 | 178 | 80 | 189 | 86 |

TABLE II

Percent Total Solids
(Grand Forks and Park River, ND 1987–1988).

|  | 1987 | | 1988 | | |
| --- | --- | --- | --- | --- | --- |
|  | Grand Forks | Park River | Grand Forks | Park River | Average |
| ND1538-1Russ | 19.4% | 19.0% | 18.0% | 22.7% | 19.7% |
| NorKing Russet | 19.9% | 20.9% | 20.9% | 22.0% | 21.0% |
| Norgold Russet | 19.4% | 20.1% | 16.9% | 20.9% | 19.8% |
| Russet Burbank | 19.4% | 18.8% | 18.6% | 19.0% | 19.0% |
| Russet Norkotah | 19.4% | 19.7% | 17.5% | 20.9% | 19.4% |

TABLE III

Percent hollow heart by weight in potato tubers 2 inches and larger in clones under test for resistance to hollow heart.

| Clone | 1986 | 1987 | 1988 | Average |
| --- | --- | --- | --- | --- |
| Norgold Russet | 36% | 28% | 0% | 21% |
| Russet Burbank | 12% | 2% | 0% | 5% |
| Russet Norkotah | 32% | 19% | 0% | 17% |
| NorKing Russet | 33% | 26% |  |  |
| ND1113-10Russ | 49% | 17% | 0% | 22% |
| ND671-4Russ | 34% | 15% |  |  |
| Krantz | 14% | 15% |  |  |
| ND1538-1Russ | 6% | 2% | 0% | 3% |
| ND2141-4Russ |  |  | 0% |  |
| ND2008-2 |  |  | 0% |  |
| ND2224-5R |  |  | 0% |  |
| LSD (0.05) | 10% | 8% |  |  |

Hereinabove has been set out a new variety of potato, *Solanum tuberosum,* identified as ND1538-1Russ including its physical characteristics and qualities. It should, however, be understood that the present disclosure is made by way of example only and that variations are possible within the scope of this disclosure without departing from the subject matter coming within the scope of the following claims, and a reasonable equivalency thereof, which claims I regard as my invention.

I claim

1. A new and distinct variety of potato plant identified as ND1538-1RUSS and deposited with the ATCC under Accession No. 75857C, deposited Aug. 10, 1994, resulting from the cross of Lemhi and ND450-3RUSS; being particularly characterized in comparison to the commercial russet potato varieties Norgold Russet, Russet Burbank, Russet Norkotah, NorKing Russet, and Krantz by the combination of traits comprising:

an upright habit of medium to large size with bushy habit; having medium green to dark green leaves and stems of green pigmentation which have purple coloration near the stem bases;

sparsely producing flowers having large corollas ranging in coloration from light lavender to white with a green midrib and having anthers with abundant orange, fertile pollen, curved styles, roughly globose, multilobed and green stigmas;

producing an average of 6 to 10 early season tubers per plant which, under normal conditions, are long, smooth, and of uniform shape, with uniform, shallow eyes, dark brown skin, a heavy russet, white flesh, and being resistant to hollow heart; and the plant being adapted to the soils of the Mid-Western United States.

2. The new and distinct variety of potato plant of claim 1 in the growth stage of tubers.

3. The new and distinct variety of potato plant of claim 1 in the form of propagating material.

* * * * *

UNITED STATES PATENT AND TRADEMARK OFFICE
CERTIFICATE OF CORRECTION

PATENT NO. : 5,434,343
DATED     : July 18, 1995
INVENTOR(S) : Johansen, Robert H.

It is certified that error appears in the above-identified patent and that said Letters Patent is hereby corrected as shown below:

At Column 3, Line 47, "75857C" should be corrected to read

"75857"

At Column 6, Line 7, "75857C" should be corrected to read

"75857"

Signed and Sealed this

Eighteenth Day of June, 1996

*Attest:*

*Attesting Officer*

BRUCE LEHMAN

*Commissioner of Patents and Trademarks*